(12) United States Patent
Le Febre

(10) Patent No.: US 7,141,152 B2
(45) Date of Patent: Nov. 28, 2006

(54) ANALYTE SPECIES SEPARATION SYSTEM

(76) Inventor: David A. Le Febre, 4665 Puerta del Sol, Camino, CA (US) 95709

( * ) Notice: Subject to any disclaimer, the term of this patent is extended or adjusted under 35 U.S.C. 154(b) by 611 days.

(21) Appl. No.: 10/389,250

(22) Filed: Mar. 14, 2003

(65) Prior Publication Data

US 2003/0226754 A1    Dec. 11, 2003

Related U.S. Application Data

(63) Continuation-in-part of application No. 09/526,920, filed on Mar. 16, 2000, now Pat. No. 6,749,735.

(60) Provisional application No. 60/364,709, filed on Mar. 14, 2002.

(51) Int. Cl.
*G01N 27/453* (2006.01)

(52) U.S. Cl. ...................... 204/450; 204/600

(58) Field of Classification Search ............... 204/450, 204/451, 454, 600, 601
See application file for complete search history.

(56) References Cited

U.S. PATENT DOCUMENTS

| | | | |
|---|---|---|---|
| 4,323,439 A * | 4/1982 | O'Farrell ................ | 204/468 |
| 4,698,142 A * | 10/1987 | Muroi et al. ............ | 204/544 |
| 5,092,972 A | 3/1992 | Ghowsi | |
| 5,151,164 A | 9/1992 | Blanchard et al. | |
| 5,180,475 A | 1/1993 | Young et al. | |
| 5,180,480 A * | 1/1993 | Manz ..................... | 204/644 |
| 5,262,031 A | 11/1993 | Lux et al. | |
| 5,282,942 A | 2/1994 | Herrick et al. | |
| 5,320,730 A | 6/1994 | Ewing et al. | |
| 5,441,613 A | 8/1995 | McCormick et al. | |
| 5,482,608 A * | 1/1996 | Keely et al. ............ | 204/452 |
| 5,728,282 A | 3/1998 | Bashkin et al. | |
| 5,750,015 A | 5/1998 | Soane et al. | |
| 5,800,690 A | 9/1998 | Chow et al. | |
| 5,810,985 A | 9/1998 | Bao et al. | |
| 5,882,465 A | 3/1999 | McReynolds | |
| 5,900,934 A | 5/1999 | Gilby et al. | |
| 5,948,227 A | 9/1999 | Dubrow | |
| 5,955,028 A | 9/1999 | Chow | |
| 5,957,579 A | 9/1999 | Kopf-Sill et al. | |
| 5,958,202 A | 9/1999 | Regnier et al. | |
| 5,958,203 A | 9/1999 | Parce et al. | |

(Continued)

OTHER PUBLICATIONS

Manz et al, J. Micromech. Microeng. 4 (1994), pp. 257-265.*

(Continued)

*Primary Examiner*—Kaj K. Olsen
(74) *Attorney, Agent, or Firm*—Thorpe North & Western LLP

(57) ABSTRACT

A analyte species separation system including a fluid flow field disposed between confining surfaces, the flow field having a first flow component flowing in a first direction and a second flow component flowing in a second, transverse, direction, and an electric field configured to cause analyte species to move in the separation flow field at least in a direction opposite to the first flow component, a analyte injection channel in fluid communication with the flow field and an analyte separation target channel or otherwise a collector in fluid communication with the flow field, the system configure so that an analyte species in an analyte sample injected into the flow field traverses at least a portion of the flow field toward the collector target channel with said second flow component, enabling analyte species separation parallel to the first direction and movement in the second direction so that analyte species having mobilities outside a selected mobility range do not enter the target channel and/or an analyte species having a selected mobility is directed into the target channel.

48 Claims, 10 Drawing Sheets

U.S. PATENT DOCUMENTS

| | | |
|---|---|---|
| 5,958,694 A | 9/1999 | Nikiforov |
| 5,959,291 A | 9/1999 | Jensen |
| 5,964,995 A | 10/1999 | Nikiforov et al. |
| 5,965,001 A | 10/1999 | Chow et al. |
| 5,965,410 A | 10/1999 | Chow et al. |
| 5,972,187 A | 10/1999 | Parce et al. |
| 5,976,336 A | 11/1999 | Dubrow et al. |
| 5,989,402 A | 11/1999 | Chow et al. |
| 6,001,229 A | 12/1999 | Ramsey |
| 6,010,608 A | 1/2000 | Ramsey |
| 6,277,258 B1 | 8/2001 | Ivory et al. |

OTHER PUBLICATIONS

Zheng Huang & Cornelius F. Ivory, Digitally Controlled Electrophoretic Focusing, Anal. Chem. 1999, 71, 1628-1632.

Robert D. Greenlee & Cornelius F. Ivory, Protein Focusing in a Conductivity Gradient, Biotechnol. Prog. 1998, 14, 300-309.

Charles R. Cantor, Cassandra L. Smith & Matthew K. Mathew, Pulsed-field Gel Electrophoresis of Very Large DNA Molecules, Ann. Rev. Biophys. Biophys. Chem 1998 17:287-304.

Peter F. Gavin & Andrew G. Ewing, Continuous Separations with Microfabricated Electrophoresis—Electrochemical Array Detection, J.Am. Chem. Soc 1996, 117, 8932-8936.

J.M. Mesaros, P.F. Gavin, & A.G. Ewing, Flow Injection Analysis Using Continuous Channel Electrophoresis, Flow Injection Analysis Using Continuous Channel Electrophoresis, Anal. Chem. 1996, 68, 3441-3449.

Stellan Hjerten, Jia-Li Liao, & Ron Zhang, New approaches to concentration on a microliter scale of dilute samples, particularly biopolymers with special reference to analysis of peptides and proteins by capillary electrophoresis, Journal of Chromatography A.676 (1994) 409-420.

J.M. Mesaros, G. Luo, J. Roeraade, & A.G. Ewing, Continuous Electrophoretic Separations in Narrow Channels Coupled to Small-Bore Capillaries, Anal. Chem. 1993, 65, 3313-3319.

Andras Guttman, Bart Wanders, & Nelson Cooke, Enhanced Separation of DNA Restriction Fragments by Capillary Gel Electrophoresis Using Field Strength Gradients, Anal. Chem. 1992, 64, 2348-2351.

Tshenge Demana, Maureen Lanan, & Michael D. Morris, Improved Separation of Nucleic Acids with Analyte Velocity Modulation Capillary Electrophoresis, Anal. Chem. 1991, 63, 2795-2797.

Cornelius F. Ivory & William A. Goble, Continuous Counteracting Chromatographic Electrophoresis, Biotechnol. Prog. 1990, 6, 21-32.

Bruce R. Locke & Ruben G. Carbonell, A Theoretical and Experimental Study of Counteracting Chromatographic Electrophoresis, Separation & Purification Methods, 18(1), 1-64 (1989).

Timothy C. Scott, Use of Electric Fields in Solvent Extraction: A Review and Prospectus, Separation & Purification Methods, 18(1), 65-109 (1989).

W. Ansorge & S. Labeit, Field gradients improve resolution on DNA sequencing gels, Journal of Biochemical & Biophysical Methods, 10 (1984) 237-243.

M.D. Biggin, T.J. Gibson & G.F. Hong, Buffer gradient gels and $^{35}S$ label as an aid to rapid DNA sequence determination, Proc. Natl, Acad. Sci., vol. 80, pp. 3963-3965, Jul. 1983C.

Dennison, W.A. Lindner, & N.C. Phillips, Nonuniform Field Gel Electrophoresis, Analytical BioChemistry 120, 12-18 (1982).

Patrick H. O'Farrell, J. Biol. Science vol. 227 Mar. 198 ? Separation Techniques Based on the Opposition of Two Counteracting Forces to Produce a Dynamic Equilibrium.

Wendy S. Koegler, Cornelius F. Ivory, Focusing proteins in an electric field gradient, Journal of Chromatography A, 229 (1996) 229-236.

* cited by examiner

ANALYTE SPECIES SEPARATION SYSTEM

This application claims priority to U.S. provisional patent application Ser. No. 60/364,709 filed Mar. 14, 2002, and is a continuation in part of the nonprovisional U.S. patent application Ser. No. 09/526,920 filed Mar. 16, 2000, now U.S. Pat. No. 6,749,735, the disclosures of which are hereby incorporated herein by reference.

BACKGROUND OF THE INVENTION

1. The Field of the Invention

The present invention relates generally to separation of analyte species in an analyte sample. More particularly, the present invention relates to a fraction collector configured for separating and collecting an analyte species from an analyte sample containing a plurality of analyte species and enabling such a separation on a continuous basis if desired.

2. Description of Related Art

The ability to separate a particular analyte species from an analyte sample is a common requirement in biological research. Likewise being able to separate a particular substance from a mixture of substances is often a requirement in pharmaceutical manufacturing. For example, the ability to separate an individual protein from a mixture of proteins is desirable in research and in the manufacturing of certain medicaments. For convenience, the terms "analyte" and "analyte species" will be used herein to refer to a sample containing a plurality of different substances, and the individual substances, respectively. Typically, these will be substances comprising molecules having a net charge (e.g. protein molecules, amino acid molecules, and DNA molecules).

HPLC, gel electrophoresis and CE typically offer a "single pass" means of separating a mixture of substances into separate substances or isolating a particular substance or group of substances. However, it is generally not efficient to do multiple separations to increase the quantity of obtained sample of one substance separated out from the sample mixture. A more efficient method is to provide a continuous separation. One method of doing this is called "Simulated Moving Bed" or SMB, which consists of switching segments of a conventional separation column in such a manner that the apparatus will allow a continuous fluid mixture including analyte to be flowing into one end of the column, and a continuous flow of a separated analyte species from the column output, while a second output discharges the remainder of the fluid mixture. Most SMB apparatus configurations comprise many packed columns, each similar to an HPLC column, for example, which are switched sequentially at time intervals to simulate a counter-flowing moving bed.

For continuous separation of analyte species, e.g. individual proteins, in complex analyte mixtures, conventional SMB processes do not work well because the HPLC columns have limited resolution, and conventional known substitutes for this method are likewise limited. Even for relatively simple analyte sample mixtures, the stationary phases used in a conventional SMB require a relatively large amount of development time to optimize the separation; and, in some instances, the stationary phase in the columns becomes very expensive.

SUMMARY OF THE INVENTION

It has been recognized that it would be advantageous to develop a system for the separation of analyte species which allows efficient separation of analyte species from analyte samples; including, but not limited to, very complex analyte samples such as blood, urine, or spinal fluid; and which can perform such separations on a continuous basis if desired. The invention accordingly provides an analyte species separation system configured to separate an analyte species of interest from other analyte species in an analyte sample. The system includes: a) a separation flow field in a fluid medium disposed between a first confining surface and a second confining surface, said flow field having a first flow component flowing in a first direction and a second flow component flowing in a second direction, said second direction being transverse to said first direction; b) an electric field configured to cause analyte species to move in the separation flow field in a direction opposite to the first direction; c) an analyte separation target channel, or collector, adjacent and in fluid communication with the flow field; and d) an analyte injection channel in fluid communication with the flow field, said analyte injection channel being disposed so that an analyte sample injected into the flow field from the analyte injection channel traverses at least a portion of the flow field toward the target channel in a direction having a vector component parallel with the second direction, and said second flow component of the flow field flowing from the analyte injection channel toward at least the target channel (collector); the system enabling analyte species to be moved in relationship to each other in directions parallel to the first direction by interaction of the first flow component and the electric field, the amount of movement being related to the mobility of the respective analyte species in the fluid medium under influence of the electric field, said analyte species being moved so as to be separated spatially in directions parallel to the first direction and also move in the second direction through the flow field so that analyte species having mobilities outside a selected mobility range do not enter the target channel and an analyte species of interest having a mobility within a selected range is directed to, and enters, the target channel or collector.

Additional features and advantages of the invention will be set forth in the detailed description which follows, taken in conjunction with the accompanying drawing, which together illustrate by way of example, the features of the invention.

BRIEF DESCRIPTION OF THE DRAWINGS

Like reference numbers refer to similar elements in the embodiment(s) shown throughout the figures.

DETAILED DESCRIPTION

Figure 1:
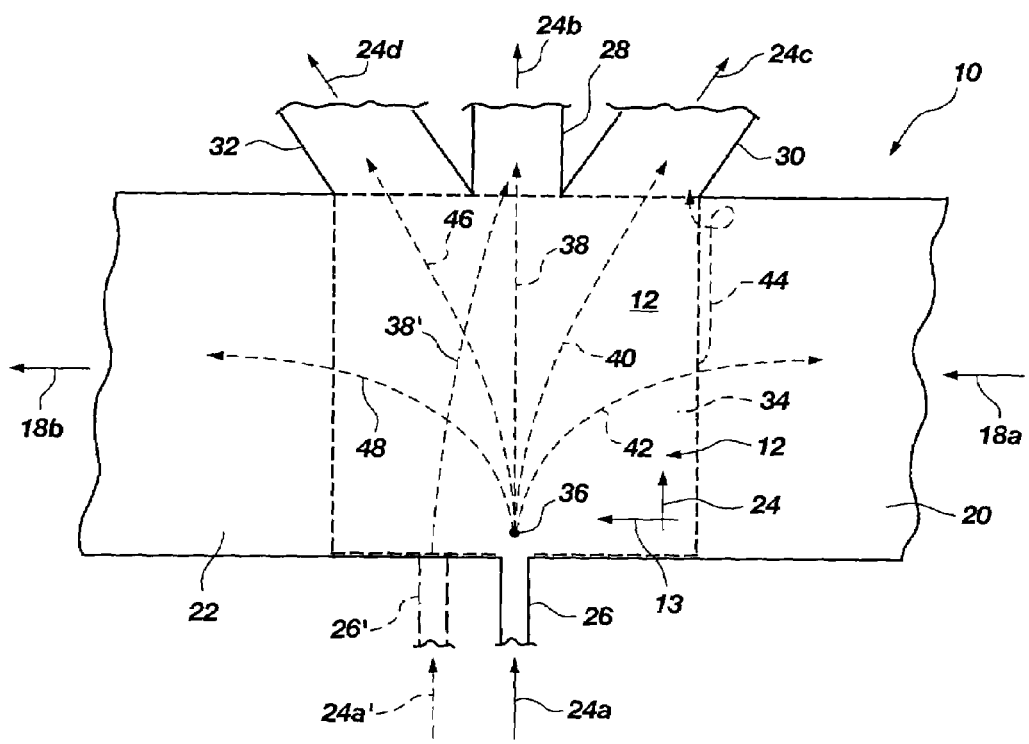
FIG. 1 is a schematic representation of a separation system embodiment in accordance with principles of the present invention, taken from a direction 1—1 above in FIG. 2.

For the purposes of promoting an understanding of the principles of the invention, reference will now be made to the exemplary embodiments illustrated in the drawings, and specific language will be used to describe the same. It will nevertheless be understood that no limitation of the scope of the invention is thereby intended. The subject matter discussed herein builds upon concepts disclosed in U.S. patent application Ser. No. 09/526,920 filed on Mar. 16, 2000, now U.S. Pat. No. 6,749,735 from which this application examples priority for the subject matter in common. As mentioned above, the disclosure of that reference is incorporated herein by reference.

Figure 2:
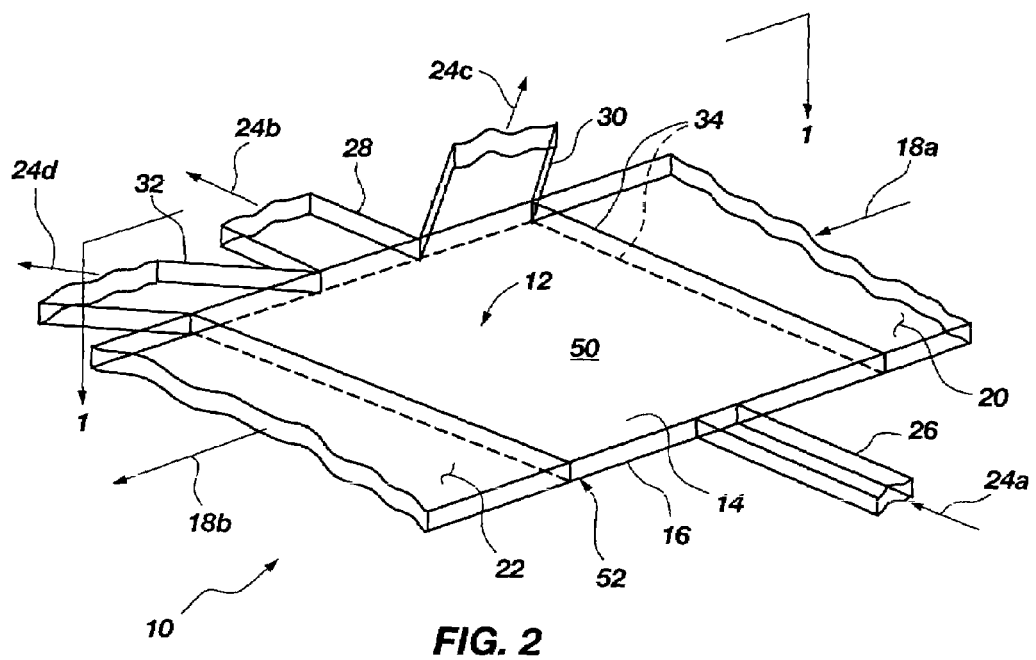
FIG. 2 is a perspective schematic view of the system shown in FIG. 1.

With reference to FIGS. 1 and 2, an analyte separation system 10 enabling continuous fraction separation and collection includes a flow field 12 confined between upper and lower confining surfaces 14 and 16, respectively. The spatial extent of the flow field can be filled with a fluid, or in another embodiment can further comprise a fluid-permeable matrix, such as a gel for example. In another embodiment, for example, the flow field can comprise a fluid in combination with a stationary phase (not shown) adjacent one of the opposing surfaces, the other opposing surface comprising a distributed resistor (as will be discussed below), the arrangement enabling additional selectivity such as chirality. A first flow component 18 comprises balanced inflow 18*a* from a first inflow channel 20 and outflow 18*b* to a first outflow channel 22. This flow can be induced by a flow generator (not shown) comprising one of a number of possible general types including a precise and controllable fluid pump, such as a syringe pump, an electroosmotic flow (EOF) generator(s) in or associated with one or both of said first channels carrying the balanced flow comprising the first flow component, or another means. The relevant consideration is that the flow component be precise as to the volume of fluid per unit time, and controlled so as to be constant or vary in a known desired way. A second flow component 24, which is also precise and controlled, substantially transverse to the first flow component, or in other words at least has a vector component orthogonal to the direction of flow of the first flow component, comprises an inflow 24*a* from a sample injection channel 26 or "injector" flowing toward and comprising an outflow 24*b* to at least a target channel 28 which can function in effect as a "collector" for analyte species of interest, and can further comprise additional outputs, for example outflows 24*c* and 24*d* to rejection channels 30 and 32, respectively. Accordingly the fluid communication location of the injection port or channel 26 comprising an injector is laterally adjacent the flow field 12 on a first side and the fluid communication location of the target channel or collector 28 is laterally adjacent and located on a second side opposite the first side of the flow field.

An electric potential is applied across the flow field 12, actually through or at least adjacent the first inflow and outflow channels, 20, 22, by means of a cathode and anode (not shown) associated therewith, and the fluid and/or a stationary phase therein is conductive to provide an electric field in the fluid as is known in the art. The electric field is configured to cause analyte species, more particularly exemplified by particles or molecules having a net charge, such as proteins, DNA molecules and DNA fragments, amino acids, colloidal particles, etc, having a charge associated therewith, to move in the flow field in a direction having a vector component opposite of a flow direction of the first flow component 18. The electric field intensity can be locally varied within the flow field to more particularly manipulate the forces on analyte species to achieve improved separation, isolation of a particular species or group of species having a mobilities within a certain selected range in the flow field due to the electric field, bring about continuous separations of analyte species of interest, and other operational and design goals.

For example, one or both of the confining surfaces 14, 16 can further comprise a contour resistor 34 which is configured to be in electrical contact with the fluid in the flow field 12. A number of discrete contour resistors can alternatively be provided. The contour resistor can provide local variation in electrical resistance in the flow field, locally varying the electric field intensity by providing a shunting current path for electrical current in the fluid. The resistance of this shunting path is made different in different locations, for example by variation of such parameters as composition, density, and/or geometry, of resistive material locally. This can be done for example by varying the thickness of the material, or varying a patterned deposition of resistive/conductive materials, or varying the composition of resistive material, to name some examples. This allows the intensity of the electrical field at each location in the flow field to be specified.

By means of these arrangements separation of analyte species can be accomplished. For example an analyte species cation 36 introduced into the flow field 12 from the injection channel 26 is acted on by at least two forces, a hydrodynamic force resulting from the first flow component 18 and the electric field acting in the opposite direction. Thus, if it has a high mobility it will move toward the first inlet channel 20, and a low mobility it will move toward the first outlet 22, in the flow field. At the same time it is acted on by the electric field and the first flow component, it is also acted on by the second flow component 24. This moves it towards the target channel 28. The system 10 is adjusted so that a selected analyte species having a particular mobility will migrate into the target channel due to the interaction of the first and second flow components and the electric field. Analyte species having mobilities above and below that of the selected analyte species, or the range of mobilities of a number of species selected, are received in the rejection channels or migrate into the first inlet or outlet channels. The salient point here being that analyte species are made to move relative to one another based on their relative mobilities in the fluid due to the interaction of the first flow component and the electric field, allowing separations.

The target channel 28 and one or more rejection channel(s) 30, 32 can lead to further collection arrangements and/or further processing steps (not shown) as will be further described below. Examples of pathways the exemplary analyte species cation 36 can follow depending on its mobility in the flow field under influence of the electric field are illustrated in FIG. 1. If the cation has a mobility within a selected range it follows generally a direct path 38 from the injection channel to the target channel 28. If it has a mobility above the selected range it can travel along a path 40 into an "upstream" or high mobility leg rejection channel 30, or even along a pathway 42 into the first inlet channel 20 wherein it can remain, or follow a path 44 toward the high mobility rejection channel. If it has a mobility below the selected range, it can follow a path 46 into the low mobility leg rejection channel adjacent but "downstream" of the target channel, or even along a path 48 into the first outlet channel 22. In one embodiment the location of the injection channel 26 is shifted "downstream" (shown as 26'), which can facilitate faster transit times for the cation in a stronger field intensity along a pathway 38' toward the target channel. These concepts will be explained in more detail below, in conjunction with citing additional specific examples.

Figure 3:
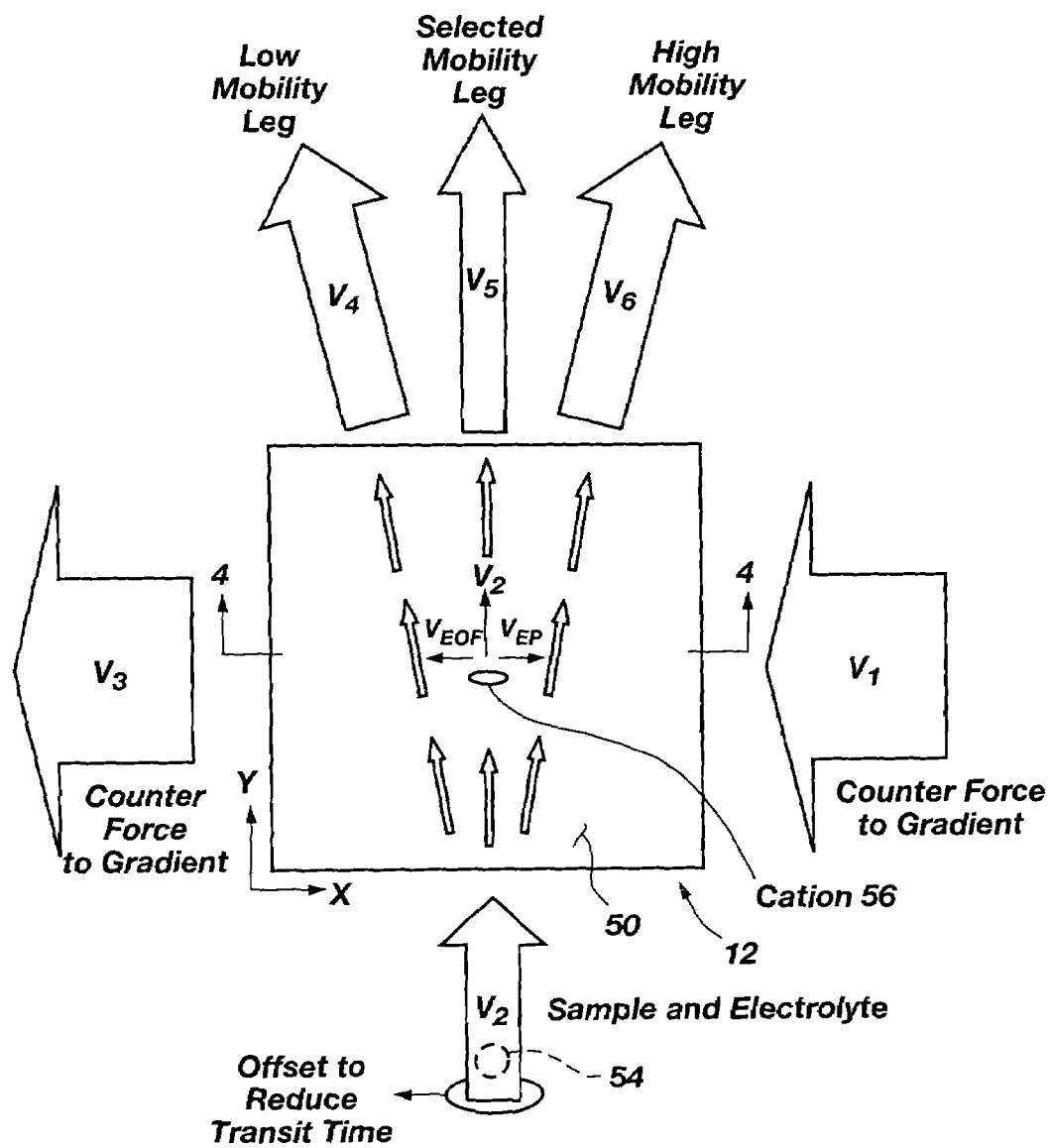
FIG. 3 is a schematic diagram illustrating principles of operation of the system shown in the FIGS.
Figure 4:
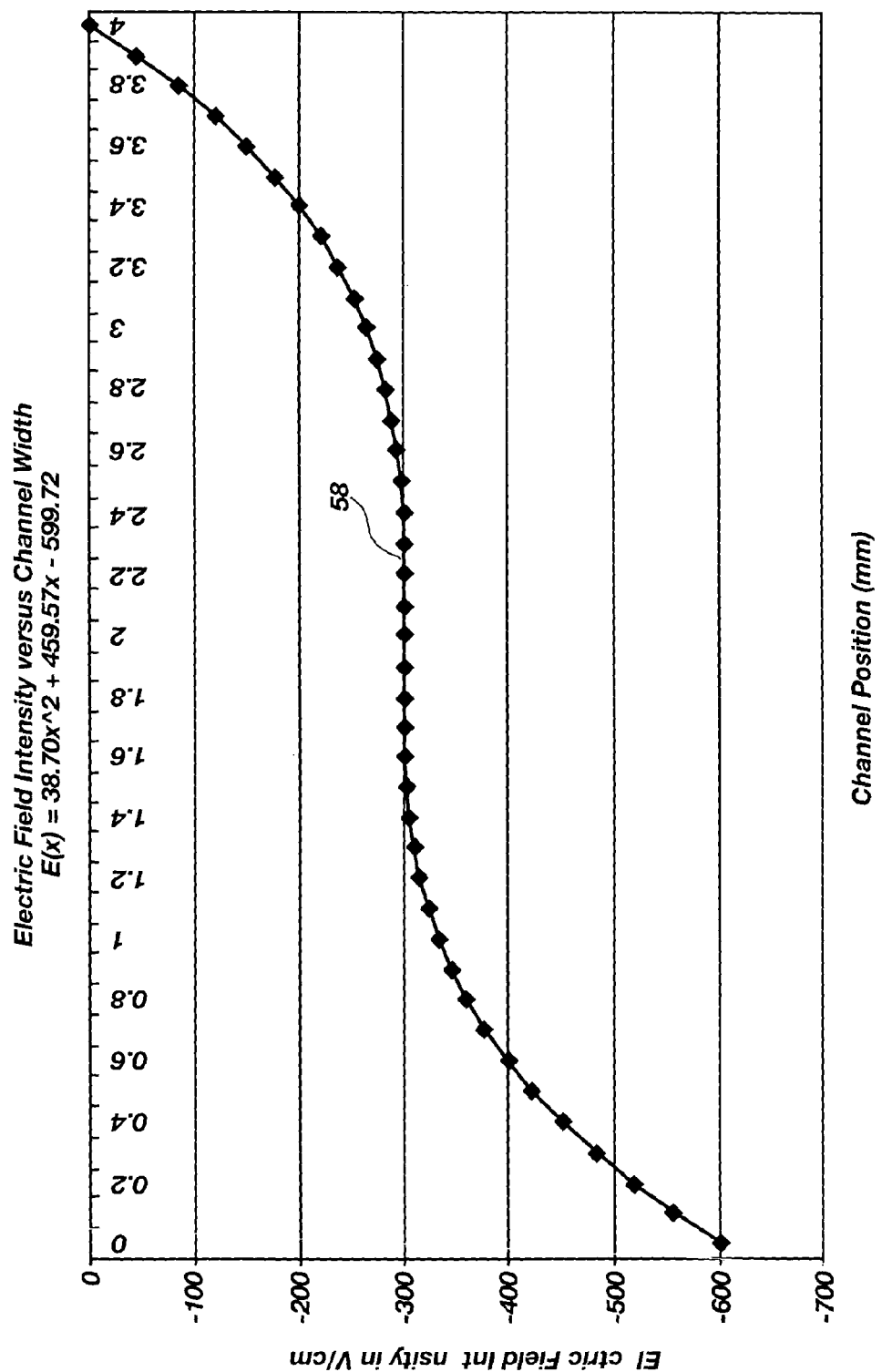
FIG. 4 is a plot of the electric field intensity profile in the separation flow field, taken along line 4—4 in FIG. 3.

With reference now to FIGS. 3 and 4 as well as FIGS. 1 and 2, it will be understood that the system 10 employs a methodology similar to electromobility focusing disclosed in the parent case to this application, but employs a second flow path. The system can be configured so that a thin cross section area comprising the flow field 12 confined between the surfaces 14, 16 contains an electric field intensity gradient continuum. This is shown as a square or parallelogram in the drawing figures, but it need not be square necessarily. In the illustrated embodiment, the counter force to the gradient, comprising a hydrodynamic force resulting from the first flow component, is constant. The flow in (V1) equals the flow out (V3) in the first inflow channel and the first outflow channel 20, 22 respectively. In another embodiment however the cross section of the channel can be variable, and as will be appreciated this results in a variable hydrodynamic counter force for the separation, and also affects the electric field intensity as the resistance of the channel changes with cross section. As an example the sides of the channel can be made to flare out or flare in through the flow field to provide an decreasing or increasing hydrodynamic force caused by the first flow component. It will be appreciated, however, that the effect on the hydrodynamic force of changing the cross-sectional area and the effect on the electrophoretic force of changing the channel the cross-sectional area tend to cancel each other out. However, flaring the walls in or out at a certain place or places can be done if it is helpful in improving efficiency of separation by providing local areas of relatively higher or lower opposing force intensities. This can be used in compensating for distortions in mobilities of protein mixtures, for example. The resistance of the contour resistor can be made locally variable, as mentioned, by variation of its thickness, patterning, locally changing its materials composition, etc. and this, in combination with variation of the cross section of the flow field 12 ,can change the electric field intensity locally as desired and provide a profile as desired. Returning to the illustrated embodiments, a "profile" of the electric field intensity, taken along line 4—4 in FIG. 3, is shown in FIG. 4.

Figure 9:
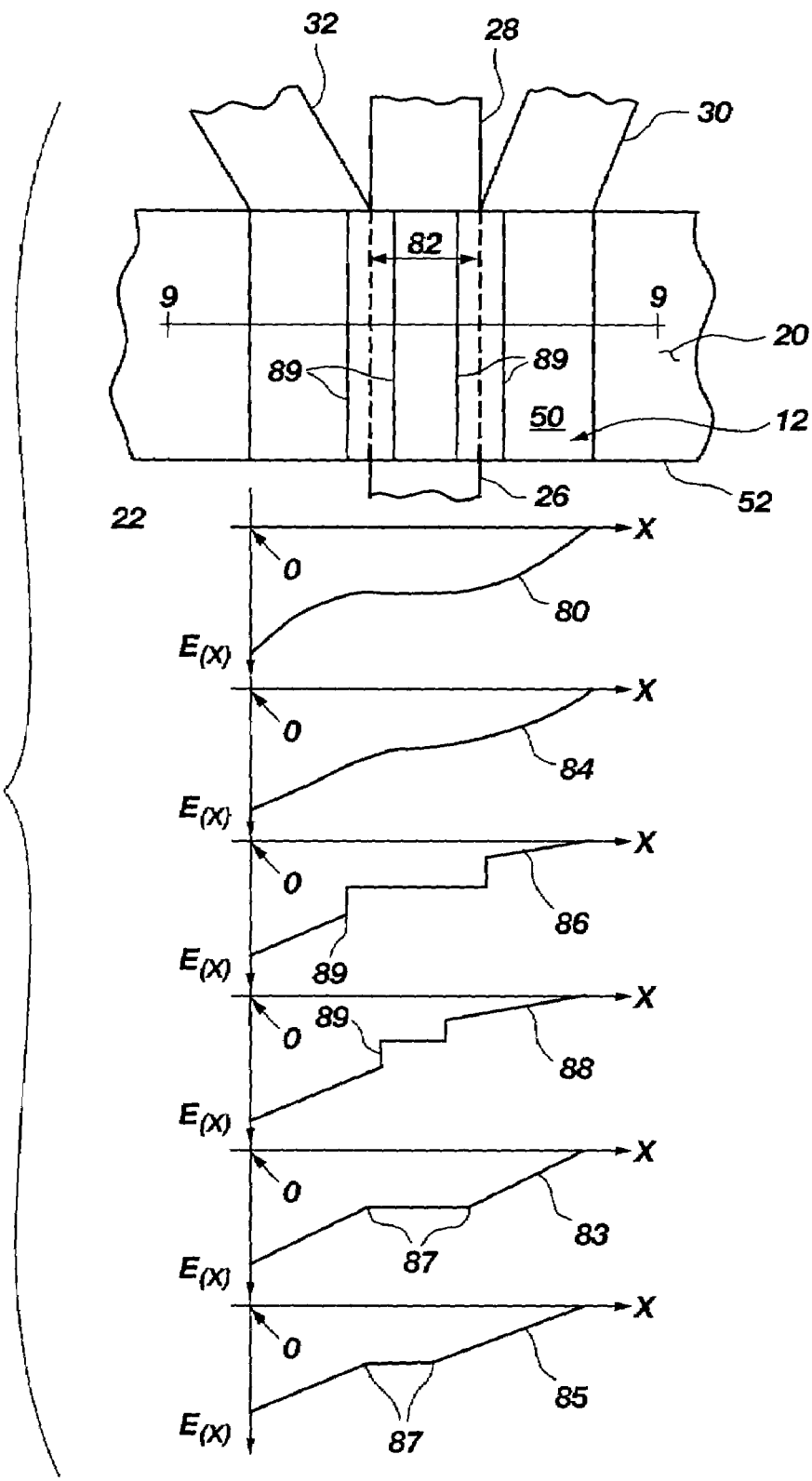
FIG. 9 is a diagram showing schematically a system as in FIG. 1, and illustrating for comparison electric field intensity gradient profiles taken along line 9—9 within the figure in additional embodiments.

The electric field intensity in this embodiment this is configured with a central "flat" section in a central portion of the flow field where the analyte species having a mobility in the range to be received in the target channel are focused. This flat portion is as long or longer than the target channel is wide. This is done so that essentially all the analyte species received in the target channel are of the "targeted" mobility. Examples of variations of this profile are shown in FIG. 9 and will be discussed below.

Returning to FIGS. 1, 2 and 3, the specifics of operation of the system 10 will now be explained in more detail with reference to an exemplary embodiment. The first flow component 18 of the flow field comprising a horizontal flow in the FIG. 3 (and comprising $V_1$ as a source and $V_3$ as a sink); and the second flow component 24 comprising a vertical flow in FIG. 3 (and comprising the inflow $V_2$ from the injection channel as a source and outflows $V_4$, $V_5$ and $V_6$ through the rejection and target channels 28, 30, and 32 as a sink). In this system 10, as in electromobility focusing disclosed in the parent application, an electric field intensity gradient is opposed by a counter flow. Thus a first force, or electrophoretic force EP induced by the electric field is opposed by a hydrodynamic force. The electric field intensity gradient increases in magnitude as x goes to zero (left side of the flow field 12 square).

In the exemplary embodiment the hydrodynamic counter force is an electroosmotic flow EOF generated in one or both of the inlet and outlet channels 20, 22; and here $V_1$ and $V_3$ are equal in flow. Unlike electromobility focusing disclosed in the parent case, a second orthogonal flow component 24 is generated, and this contains the sample mixture. This flow has the condition that $V_2$ equals $V_4$, $V_5$ and $V_6$. Here again, in one embodiment all flows in the injection channel and target and rejection channels are electroosmotically generated. Thus, two orthogonal flow components coexist within a chamber defined by the first and second confining surfaces 14, 16 comprising top and bottom surfaces of a channel 52 and sides of the channel, and coextending with a variable resistance contour resistor 34 disposed on at least one of the confining surfaces. In an exemplary embodiment, the chamber is about 4000 μm by 4000 μm and about 50 μm high. This defines the volume of the flow field. Both of the confining surfaces are dimensioned at about 4000 μm by 4000 μm and embody contour resistors. These are configured to locally vary in their resistance, but vary only in the x-axis direction. Control surfaces (not shown) to establish the EOF for precisely controlled flows to establish the hydrodynamic counter force for separation and the flow component for moving the sample through the flow field are located in each of the six "legs" comprising the first and second inlets and outlets 20, 22, 26, 28, 30, 32 but not in the square chamber 52 confining the flow field 12 itself. The electric field intensity gradient is generated by an isolated power supply (not shown), which also generates EOF flows $V_1$ and $V_3$ using control surfaces in each of the legs. Another power supply (not shown) referenced to ground generates $V_2$, $V_4$, $V_5$ and $V_6$.

A sample mixture comprising individual proteins and electrolyte is moved into the flow field with a velocity determined by the control surfaces of leg 2 comprising the injection channel 26. Once the individual proteins are within the square chamber 52 flow field 12, the proteins are affected by three independent forces: a hydrodynamic force comprising the second flow component comprising V2; the electric field intensity gradient; and the first flow component comprising the hydrodynamic counter force comprising V1. The gradient and counter force will cause a protein 56 traveling within the flow field to reach an x-axis equilibrium position as it travels along the y-axis. Once the protein reaches the upper part of the flow field square in FIG. 3, the protein will enter one of three ports (28, 30, 32 in FIG. 2) depending on where along the x-axis it reached equilibrium within the electric field intensity gradient and hydrodynamic counter force regime in the flow field.

Figure 5:
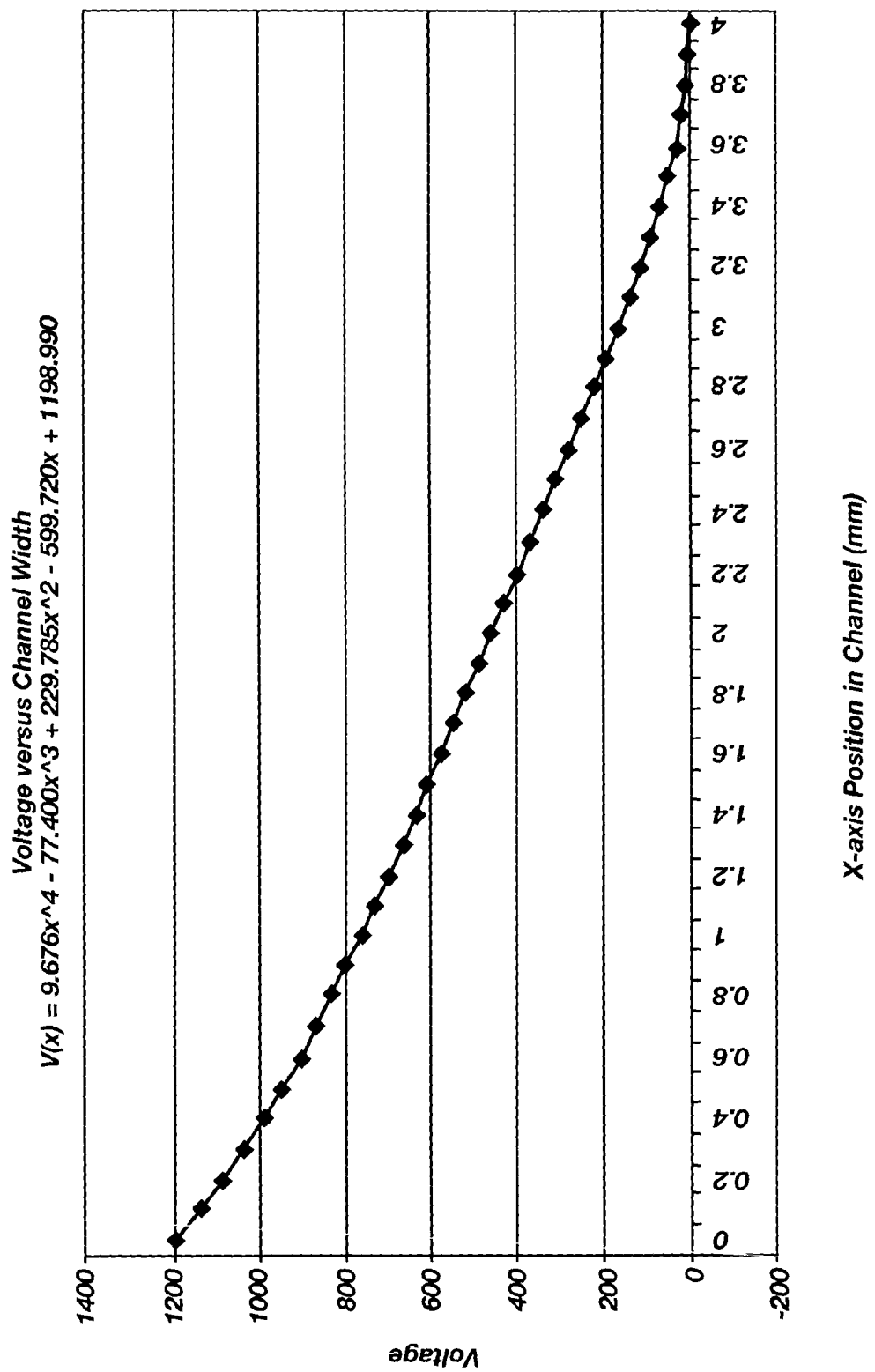
FIG. 5 is a plot of voltage along the same profile as in FIG. 4.
Figure 6:
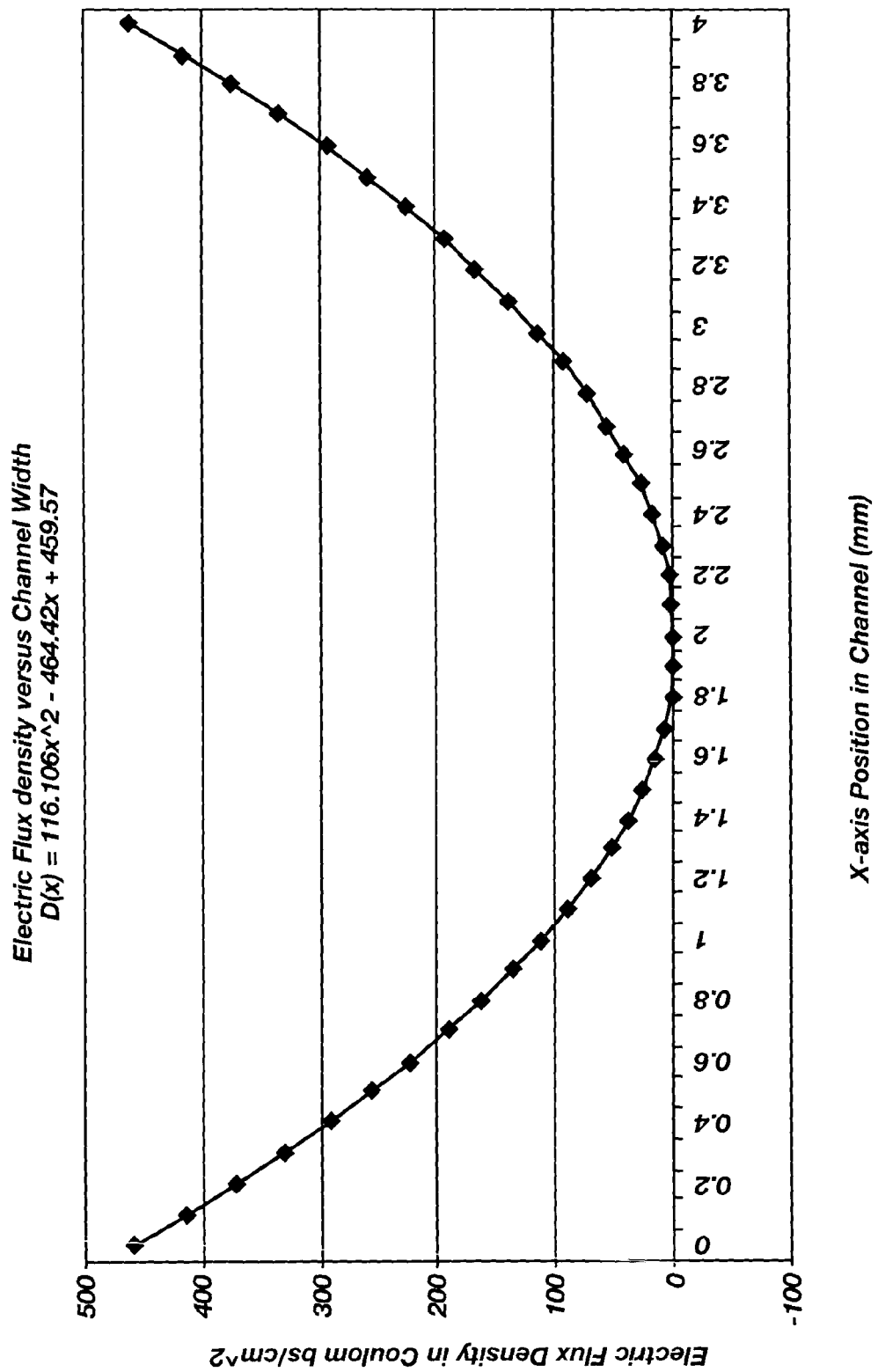
FIG. 6 is a plot of electric flux density in coulombs per square centimeter along the same profile as in FIG. 4.

As shown in FIG. 4, an electric field intensity gradient profile 58 across the flow field 12 in the x-direction has a constant electric field intensity band in a middle portion (x=2000 plus or minus about 500 μm) and increasing electric field intensity to the left (x=2000 µm to x=0 µm) and decreasing electric field intensity to the right (x=2000 to x=4000 µm) of the band. The curve has a near zero slope in this band midway along its length. As will be appreciated, the result of variation in resistivity of the contour resistor in the x-direction. A plot of voltage with x-axis position along line 4—4 is shown in FIG. 5, the electric field intensity being the derivative of the voltage; and, with reference to FIG. 6, it is seen that the electric flux density plot shown, which corresponds with the derivative of the field intensity, E (x), gives the shape of the electric field intensity gradient profile. With reference again to FIGS. 1–3, For the continuous separation of a given protein 56, the velocity of the fluid creating the hydrodynamic counter force, made up of $V_1$ (source) and $V_3$ (sink) is set so as to be equal and opposite to that which is imparted to and acts on the protein molecules generated by the protein's mobility multiplied by the central electric field intensity (middle band of say 300 V/cm shown, for example). This selected protein is then driven into leg 5, the target channel 28. Proteins with mobilities less than the selected protein are routed to leg 4, a rejection channel 32, and proteins with higher mobility are routed to leg 6 comprising the other rejection channel 30.

The contour of the electric field intensity gradient to a great extent determines the degree of selectivity the system 10 has to the desired protein, or in other words, how efficiently the selected protein will be isolated, and how effectively the other proteins are rejected. The cooperation of the electric field and the counter force produces the force regime which influences, among other things the speed of the separation process in the x-direction. The electric field intensity gradient continuum with counter force accordingly provides the means to separate a selected protein (or a group of proteins having similar mobilities) from a sample mixture 54 including other proteins. The profile of the electric field intensity gradient shown in FIG. 4 is the plot of a third order polynomial $E(x)=38.70 \; x^3-232.21x^2+459.57x-599.72$ which is symmetric to the y-axis center line (x=2000 µm) and provides equal rejection of proteins with mobilities above and below the selected protein mobility. The voltage required to generate the electric field intensity is the integral of $E(x)$, which is $V(x)=9.676x^4-77.400x^3+229.785x^2-599.720x+1198.990$, as seen in FIG. 5. The electric flux density, $D(x)$ is the derivative of $E(x)$ and is plotted in FIG. 6. As will be apparent from FIG. 6, the magnitude of the slope of the function $E(x)$ is nearly zero at x=2 mm but increases on either side. The ability to reject a protein that has a mobility that is close to the selected analyte protein is determined by the rate of change of the electric field intensity gradient at and near the center of the flow field where the target channel is located. The objective is to have a minimal change in slope in the center to spatially separate similar mobility based proteins further apart in the x-axis direction. However, counter to that need is the requirement for a shape gradient, to increase the speed of the separation. The first requirement determines resolution, and the second requirement determines throughput of the system 10.

Figure 7:
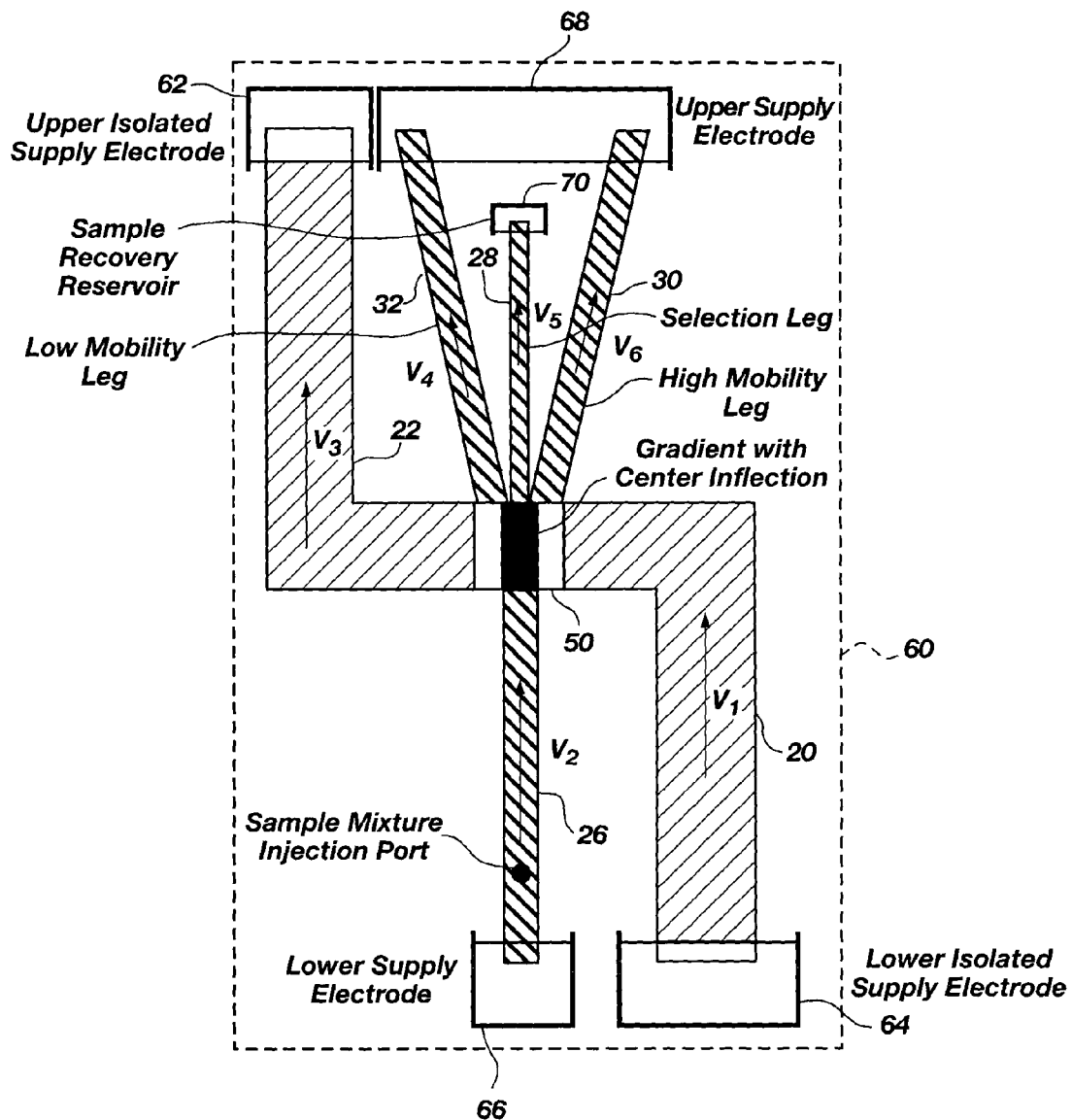
FIG. 7 is a schematic diagram illustrating the system of FIGS. 1–6.

Continuing with description of an exemplary embodiment, with reference to FIG. 7 the block diagram illustrates features of a continuous fraction collector system 60. Leg 1 and Leg 3 comprising the first inlet and outlet channels 20, 22 are a total of about 4 cm long (including the separation flow field chamber 50) and have a voltage drop of 600 V/cm. From an isolated upper supply electrode 62 to the lower isolated supply electrode 64 the voltage drop is 2,400 volts, with 1200 volts applied to the upper isolated electrode and −1200 volts applied to the lower isolated electrode. Leg 1, the inlet channel 20, is slightly longer than Leg 3, the outlet channel 22, to compensate for the asymmetric voltage drop across the chamber 50. This results in a voltage drop at x=2 mm in the chamber of zero volts.

Since both power supplies for Legs 1 and 3 are isolated, the electrolyte flowing in either leg is the same, and the first flow component 18 comprises a volume of flowing fluid confined only to these two legs. The amounts of leakage current across the supply transformers determine the amount of electrolyte fluid cross flow into Legs 2, 4, 5 and 6. If the supplies are isolated at the primary transformer, the leakage current is minimal. For example, using a low leakage current transformer (115 volts to 24 volts available commercially from Advanced Components Industries, Inc. Torrance, Calif., Part Number 0142400-1-0000), followed by a DC to DC converter of 24 volts to 2500 volts) the current leakage is less than $1\times10^{-9}$ amps with 5000 volts DC applied to the primary or secondary. For a typical current of 0.5 to 5 milliamps flowing in Legs 1 and 3, the DC leakage current is 1,000,000 times less than the Leg current, resulting in virtually no electrolyte fluid volume comprising the flow through legs 1 and 3 flowing into the other legs, or fluid volume from the other legs being drawn into the flow from Leg 1 to leg 3. Legs 2, 4, 5 and 6 are driven by the lower supply electrode 66, the upper supply electrode 68 and the sample recovery reservoir electrode 70. The voltages of the upper supply electrode and the recovery reservoir electrode can be biased to the same value. The voltage drop required across these later-mentioned leg segments is dictated by a minimal electric field intensity sufficient to drive the system, e.g. 100 to 300 volts/cm. If all of the legs are 4 cm long, then the lower supply electrode is −800 volts and the upper supply electrode is +800 volts for an electric field intensity of 200 V/cm. The selected voltages place the center of the chamber 50 in the y-direction at near zero volts and a total voltage swing across the y-axis of +/−80 volts and the x-axis of +800 volts to −400 volts.

A reasonable required design residence time in the flow field 12 of a protein cation 56 is the time required for it to propagate from one side (y=0 µm) of the chamber 50, to the opposite side (y=4000 µm). A minimum design residence time is established by the slowest protein's orthogonal (x-axis) propagation from the center of the flow field in the channel chamber in the x-direction to the x-axis location of low mobility branch (leg 4) rejection channel 32. To improve throughput the input (leg 2) comprising the injection channel 26 is intentionally offset "downstream" on the x-axis to reduce this lateral transition time. (This possibility is illustrated in FIGS. 1 and 3) By allowing offset of the center of the injection channel comprising leg 2 the transition time can be established by an offset distance (x-axis distance from leg 2 to leg 5) and the mobility of the selected protein. The selected protein then will follow a diagonal course from leg 2 comprising the injection channel, to let 5 comprising the target channel 28.

The selected protein's mobility can be altered by changing the pH of the electrolyte away from the isoelectric point of the selected protein to increase the mobility of the protein and hence reduce its residence time in the flow field 12 in the chamber 50. The propagation time of the selected protein from the injection channel, leg 2, to the target channel, leg 5, is determined by its mobility and the electric field intensity (in this case 300 V/cm). Therefore, if, for example, the width of the outlet into the flow field of leg 2 and inlet to leg 4 is 200 µm, then the worst-case lateral (x-axis) travel of the selected protein is 200 µm or for a protein with a mobility of $1\times10^{-5}$ cm/V-sec, and the time to travel the required 200 µm is 6.6 seconds. This then establishes that a sample source fluid velocity, V2, in the must be chosen so that the analyte species protein of interest has a minimum time to transit the specified diagonal distance across the flow field in the y-direction and across the required x-direction offset, if any, of at least 6.6 seconds. In the example, the diagonal distance between leg 2 and leg 5 is a diagonal line of 4.005 mm resulting in a velocity of 0.607 mm/sec (0.0607 cm/sec). This corresponds to a volume of (200 µm×50 µm×4000 µm) or $40\times10^{-12}$ cubic meters or 40 nL per 6.6 sec or 6.06 nL/sec or 21.8 µL/hr or 523.2 L/24 hrs. Optimizing the pH to increase the selected protein's mobility could potentially increase the separated volume by a factor of 10 in some cases. Also, decreasing the width of Leg 3 and Leg 5 decreases the x-axis travel distance with a corresponding increase in throughput.

The degree or efficiency of rejection is governed by the difference in the electric field intensity gradient between leg 4 and leg 5 and between leg 6 and leg 5. For an inflected gradient where the center of inflection corresponds with a centerline of leg 5, the differential gradient is about the same. However, in practice there is not true symmetry since the lateral forces ($V_1$ and $V_3$) are biased by E(x).

Continuing with the example, for separation of a protein with an electrophoretic mobility of $1\times10^{-5}$ cm²/V-sec the counter force ($V_1$ "source" and $V_3$ "sink" flow) is $3\times10^{-3}$ cm/sec. At 1.9 mm (x-axis) the electric field intensity is −299.6329 V/cm resulting in a lower limit of mobility of $1.00122\times10^{-5}$ cm²/V-sec and at 2.1 mm the electric field intensity is 300.5267 V/cm resulting in an upper limit of mobility of $0.99825\times10^{-5}$ cm²/V-sec. This results in a differential mobility window for leg 5 with a width of 200 µm of $2.97\times10^{-8}$ cm²/V-sec.

In separating protein samples 54 with very low concentrations, the width of the target channel 28 comprising leg 5 may be substantially reduced resulting in a corresponding increase in selectivity. In example set forth above, decreasing the width of the opening into the target channel comprising leg 5 from 200 µm to 20 µm decreases the mobility width of the window to 2.97×10−9 cm/V-sec.

Figure 8:
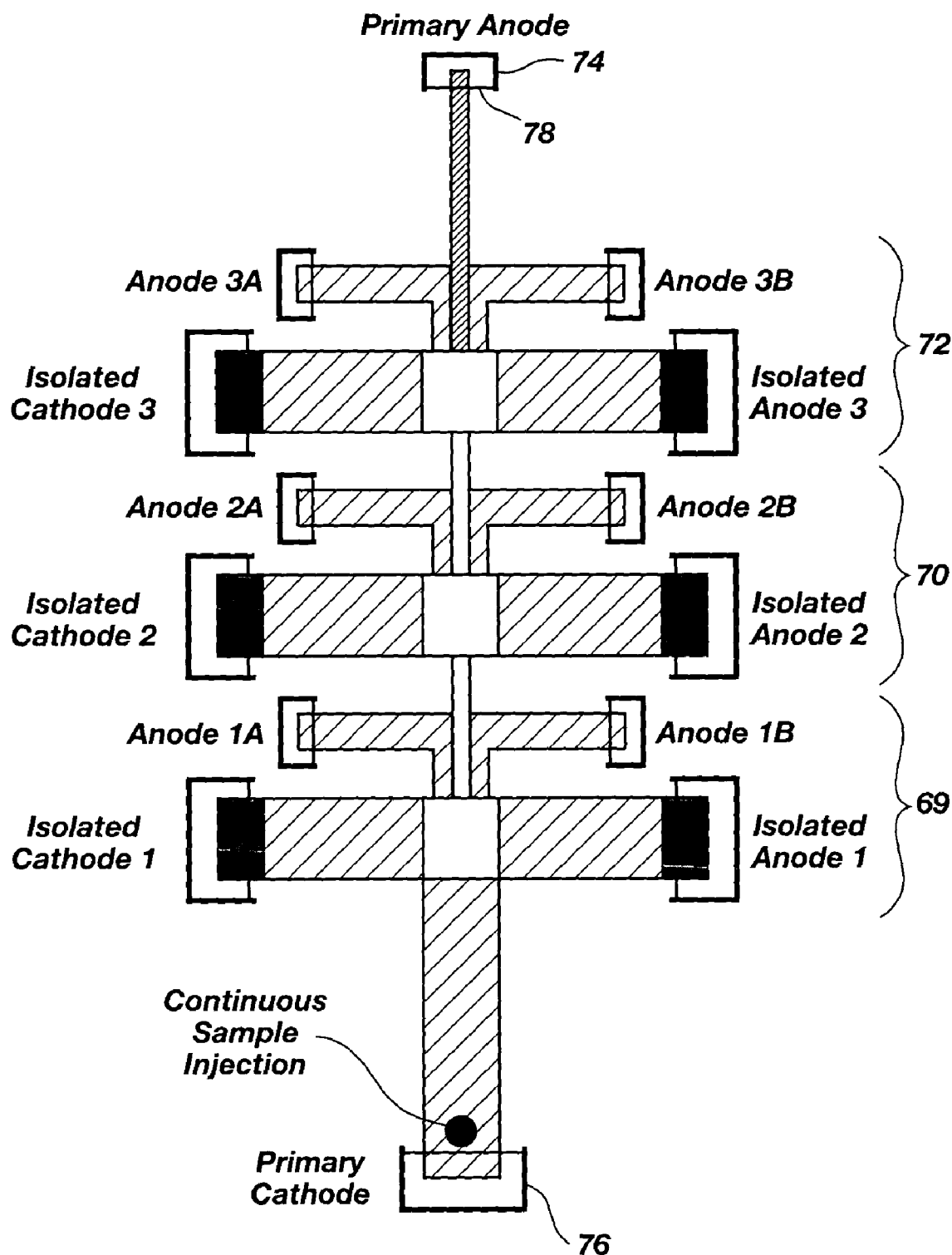
FIG. 8 is a schematic diagram of an embodiment incorporating a plurality of separation stages.

With reference to FIG. 8, for higher protein selectivity additional stages 70, 72 may be added to the system 10'. In the illustrated example a three-stage configuration is shown. The first stage 69 is essentially as the system 10 has been described above with a gradient spanning 0 to 600 V/cm over a 4 mm distance. A second stage 70 has an electric field intensity gradient continuum that spans a range of 290 V/cm to 310 V/cm. A third stage 72 spans a range of 299 V/cm to 301 V/cm. If the three stages have the same electric field intensity gradient profile, a decrease in the range of the electric field intensity gradient increases the selectivity. For example, stage 2 would have a mobility selectivity that is 30 times higher than stage 1, or $9.9\times10^{-10}$ cm 21V-sec for a protein with a mobility of $1\times10^{-5}$ cm2/V-sec; and stage 3 has a mobility selectivity that is 10 times higher than stage 2, or $9.9\times10^{-11}$ cm2/V-sec. In stage 2 and stage 3 the protein mobility range of the electric field intensity gradient provided in the flow fields is successively narrowed by decreasing the resistivity of the materials used in the contour resistors in the confining surfaces 14, 16 of the chambers 52. This can be done for example by laying down a patterned resistive material by a printing process and altering the pattern laid down and/or altering the resistivity of the ink or in other words the resistive material used. The resistivity of the electrolyte can be the same for each stage, simplifying design and operation.

As will be appreciated, each stage is provided with isolated cathodes and anodes connected to isolated power supplies, for the same reasons as discussed above, including isolating flow components in the flow fields and minimizing cross flows. The second flow component in each and all the stages 69, 70, 72 in the exemplary embodiment illustrated is controlled by the EOF induced in the y direction through the system by the primary anode 74 and cathode 76. A sample recovery reservoir 78 is associated with the primary anode. In another embodiment, isolating each anode and cathode can be done, and this allows greater design flexibility, and flexibility in operation, as it is possible to selectively provide different isolated voltages across different pairs of anodes and cathodes throughout the system.

As mentioned above, a sufficiently precise small volume pump (not shown) can also be used in each case to provide the hydrodynamic flow in each of the stages and/or to provide the second flow component in each case, some cases, or in all cases, to move the sample through the successive stages.

In other embodiments, it is also possible to change the profile of the electric field intensity gradient for each successive stage to further increase the separation power of the device and/or change the width of the sample target channel and/or the size and shape of the flow field in each of the following stages to increase throughput or increase resolution. Also, depending on whether it is desired at a particular stage to pass all of an analyte species in the sample, even if it means also passing at least some other analyte species having similar mobilities, or it is desired to pass on only a desired species or group of species, even if some of the selected analyte species is "lost" to rejection channels, the profile of the electric field intensity gradient with respect to the x-axis can be altered to facilitate these goals.

For example, as shown in FIG. 9, if the goal is to select only a desired species or group of species having a selected mobility or mobility range, then a profile 80 along line 9—9 in the figure is desirable as it is flat or nearly so across the width 82 of the target channel 28. As discussed the width of the channel can be decreased to enhance this effect. Some spillover of selected species cations into the rejection channels is possible, even likely. Alternatively, if in the stage in question only a culling of the greatly different mobility species is desired an it is desired to pass essentially all the analyte species of interest to the next stage, a profile similar to the profile 84 shown just below the last discussed profile in the figure can be used. Since the flat portion of the profile, corresponding to the equilibrium location for the species of interest, is entirely within the width of the target channel, essentially all of that species would pass, while the sample will be reduced by the relatively high and low mobility species removal.

Also, unlike electromobility focusing where generally speaking a field intensity continuum, that is to say a smooth function, is desirable, in a staged system discontinuities can be helpful to enhance spatial separations. For example, profiles 83, 85, 86, and 88 are similar to profiles 80 and 84 just discussed but a sharp or sudden change in slope 87 or a discontinuity 89 provides a more definite and locatable "bright line" separation feature enabling the edges of the mobility range in question to be more positively located with respect to the target channel, so as to be well inside, well outside, or substantially correspond with the width extent of the target channel. The discontinuity can comprise a sudden change in conditions in the flow field, for example a sudden change in the width of the channel 52 carrying the first flow component within the chamber 50, or a conductive strip interrupting the contour resistor where an isolated potential is applied to suddenly shift the profile 86, 88, to name a few examples. As will be appreciated however, in practice a precise and sharp change in the field intensity providing such a "bright line" is difficult to achieve. But an approximation provided by this embodiment can in some cases provide substantially the functionality just described.

It should also be noted that in another embodiment the rejection channels could also be connected to further stages for additional processing, allowing for a branch approach to separation of multiple mobility species. Also, it will be apparent that collection reservoirs (not shown) can be provided at a termination of the rejection channels, and sample collected there can be transferred to another similar system for further separations. Such a branching approach can potentially enable isolation of a large number of separate analyte species, even in a relatively large throughput and/or continuous process application.

Returning to FIG. 2, the configuration of the contour resistor 34 is determined using the same mathematical method as disclosed in the parent case in electromobility focusing. If the contour resistor is generated using a plotting process using multiple pens such as the OHMCRAFT™ MICROPEN™ made by Ohmcraft of Honeoye Falls, N.Y., then each drawn line in the y-axis represents a single resistance with a spatial resolution of up to 0.025 mils (0.635 microns). However, to get a desired resistivity usually requires that at least two inks be blended on top of each other to achieve a smooth resistance gradient between lines. The inks can also be blended for each line before entering the pen.

Another approach is to lay down the resistor by use of a multi-ink (similar to multi-color) ink jet print head to deposit multi-compositional (different ink resistivities) drops to produce the x-axis resistance gradient. Thus to get a specific dot resistance, multiple drops are deposited on top of one another and diffuse together to form a composite. Therefore, each line in the y-axis has the same resistance but adjacent lines have slightly different resistances. There is also diffusion between lines to smooth the resistance profile in the x-axis. As an example, a computer-controlled plotter would perform the ink deposition by incrementing an x-y platform and the ink can be deposited from 8 different ink jets (100 ohms/square, 1000 ohms/square, 10,000 ohms/square, 100 kilohms/square, 1 megohms/square, 10 megohms/square, 100 megohms/square, and 1000 megohms/square). Each drop can consist of two or more inks. Each ink jet would generate a 10 µm diameter drop, which should be positioned within a spatial location of +/−1 µm. A 4000 µm×4000 µm planar contour resistor can comprise 160,000 dots (10 µm diameter) and at a rate of 100 dots per second (per row) and 1 second to switch between rows such a contour resistor would require less than an hour to deposit on a substrate forming the confining surface 14 or 16. Carbon-doped thermal set epoxy inks are commercially available. For example, such inks can be obtained from Metech, Inc. of Elverson, Pa. which product nos. 8511 through 8561, for example, correspond with resistivities of 10 ohms/square to 10 megaohms/square.

In another embodiment the contour resistor can be formed using photo-resist and/or thin film techniques to provide improved resolution. Ion implantation such as used in semiconductor manufacturing processes can also be used to provide increased resolution. However, the cost of manufacture can also rise with these techniques, and they typically require a large production quantity to be economical. Commercial-scale production of a disposable system for a widespread testing application can employ one or more of these latter techniques for example.

Figure 10:
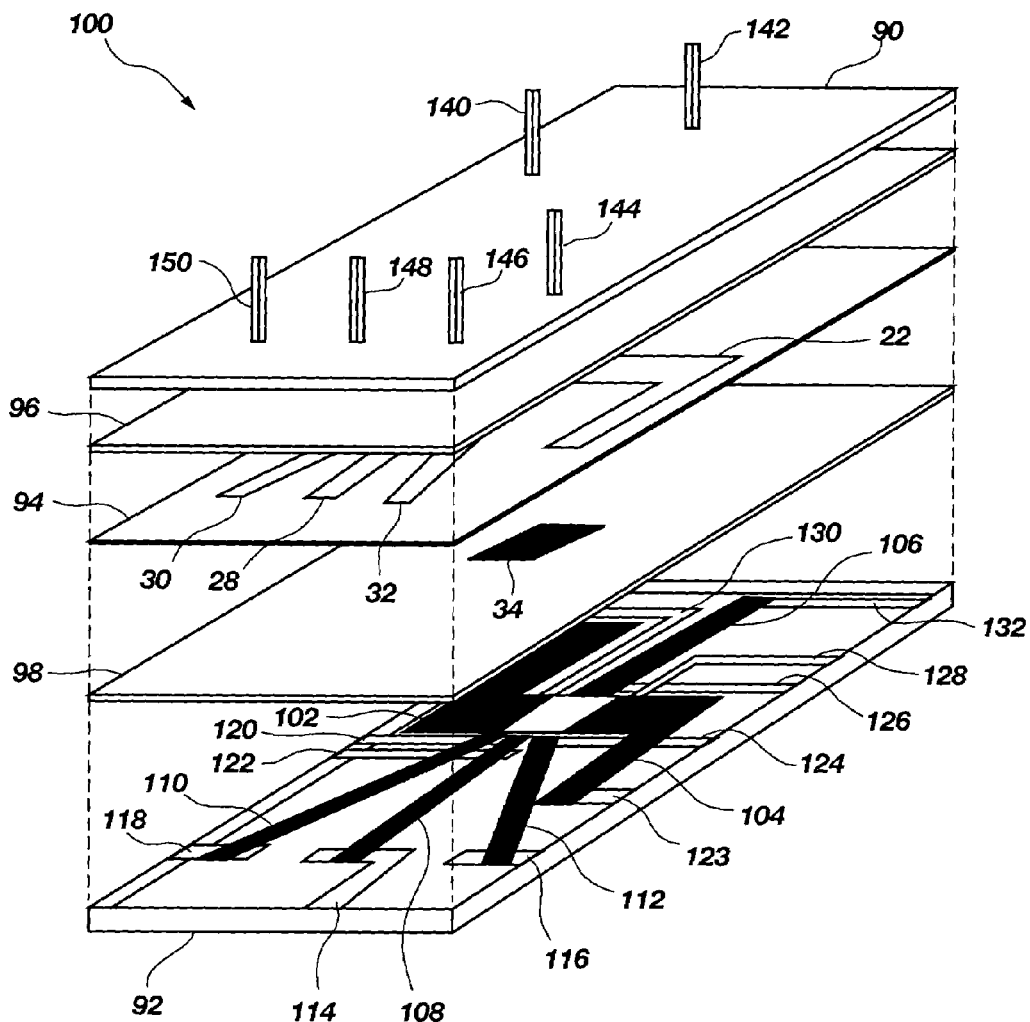
FIG. 10 is a perspective exploded view of a separation device embodying the system in accordance with principles of the invention illustrated in FIG. 7.

With reference now to FIG. 10, in an exemplary embodiment a configuration of a continuous fraction collector device is illustrated. The device can be fabricated in essentially the same manner as the electromobility focusing device disclosed in the parent application. Two refractory substrates 90, 92 are used to form the top and bottom of the assembly 100 and a spacer 94 having a cut-out pattern conforming to the channel configuration is used to form the channels 20, 22, 26, 28, 30, 32, etc. and the chamber 50 discussed above is disposed intermediate the substrates. The spacer in one embodiment is PTFE that is sintered and filled with glass particles. The spacer is die cut to form the channels. The spacer is typically 0.002 to 0.003 mils (50 to 75 microns) in thickness.

Each substrate 90, 92 has thick-film distributed resistors 102, 104, 106, 108, 110 and 112 corresponding to the channels 20, 22, 26, 28, 30 and 32, respectively, discussed above, screen printed thereon in mirror-image fashion. These comprise EOF control surfaces disposed above and below and essentially co-extensive with, the channels, to provide flow control. In another embodiment where precisely controlled pumps are used for flow control these control surfaces can be eliminated, simplifying the configuration. Returning to the illustrated embodiment, conductors, referenced by even numbers 114–132, are also screen printed on the inner surfaces of the substrates in essentially mirror image fashion. Dielectric bridges between conductors and distributed resistors and other conductors where they cross but need to be electrically isolated are also laid down. The printing processes are followed by deposition of high K dielectric layers 96, 98 over the substrates. The high K dielectric layers form the upper and lower portions of the channels and the spacer defines the sides and height extent of the channels. The contour resistors 34 defining the confining surfaces 14, 16 are deposited on the dielectric layers 96, 98 as discussed above. In an alternate embodiment the dielectric layers can be separate layers which are attached to the printed substrates. In assembly of the device 100 the substrates with dielectric layers thereon are sandwiched together with the spacer located intermediate the two substrates. As will be appreciated, precision in registration of the printing processes and layer assembly is important.

The substrates 90, 92 are made from material comprising 97% alumina. In the illustrated embodiment they are 0.125 to 0.25 inches thick. In one embodiment they are lapped smooth and the inner surfaces prepared so as to be suitable for thick or thin film deposition by screen printing. As discussed, subsequently screen-printed on the substrate are the distributed resistors 102–116, and dielectric bridges (not specifically shown, but present between crossing elements as required) followed by conductors 114–132, which form electrical contact with the distributed resistors and provide a means to electrically drive the conductors from the exterior of the device. On top of these screened resistors and conductors in each case is deposited the dielectric layer 96, 98 which actually can comprise three or more layer depositions of thermal-set filled epoxy (each layer is 14 to 25 microns thick). The epoxy is loaded with 30 to 50% 0.5 to 5.0 micron $BaTiO_2$ powder. The high K filled epoxy further comprises a resin and an aliphatic amine curing agent. At room temperature it has a volume resistivity of $1\times10^{15}$ ohm-cm and a surface resistivity of $5\times10^{16}$ ohm-cm. The $BaTiO_2$ powder is thoroughly mixed into the epoxy and out-gassed before the screening operation. Each layer is cured at 225 degrees C. prior to the screening of the next layer. After curing the filled epoxy, the contour resistors 34 are deposited on top of the dielectric.

It should be noted that each successive layer is fabricated using a lower temperature than the previous layer. The alumina substrate has the highest continuous use temperature of over 1200 degrees C., followed by the inorganic thick film distributed resistors and conductive inks, which are processed at 850 to 875 degrees C., followed by the thermalset filled epoxy, which is processed at 250 degrees C. and finally the contour resistors, which are processed at 220 degrees C.

As discussed, the upper and lower substrates are mirror images of each other; however, the upper substrate 90 has thru holes formed in the alumina substrate, and the upper dielectric layer likewise has openings formed therein for fluid connections to the various channels discussed. KOVAR tubing segments 140, 142, 144, 146, 148 and 150 for the various connections are disposed in the holes in the substrate, which arrangement allows for the attachment of plastic tubing to carry electrolyte and the sample to and from the channels, reservoirs, etc.

In assembly the spacer 94 is precisely placed over and onto the structure of the lower substrate 92 and dielectric layer 98 over a layer of adhesive. The upper substrate assembly 90, 96, etc. with an adhesive layer thereon is precisely located over and placed onto the spacer, and they are brought together. clamps are subsequently secured around the assembly and the resulting sandwich is compressed. In one alternative embodiment this procedure is done using instead a 5-mil heat tolerant sheet spacer with adhesive deposited on each side, like a double-sided tape, which is die cut to provide the fluid channel configuration. In another embodiment a known thickness of epoxy is screened onto a substrate assembly over the other layers deposited, and spheres of uniform diameter matching the desired thickness of the spacer are either contained in the uncured epoxy or are added to at least the peripheral locations of the uncured epoxy. After the other substrate has been placed on top in proper registration, pressure and heat are applied to cure the epoxy. In another alternative, the spacer can be provided by a die-cut thermal plastic layer, which is heated between the substrates while pressure is applied. The plastic is heated sufficiently above the use temperature so as to soften so as to adhere to the upper and lower substrates on either side, then cooled.

Figure 11:
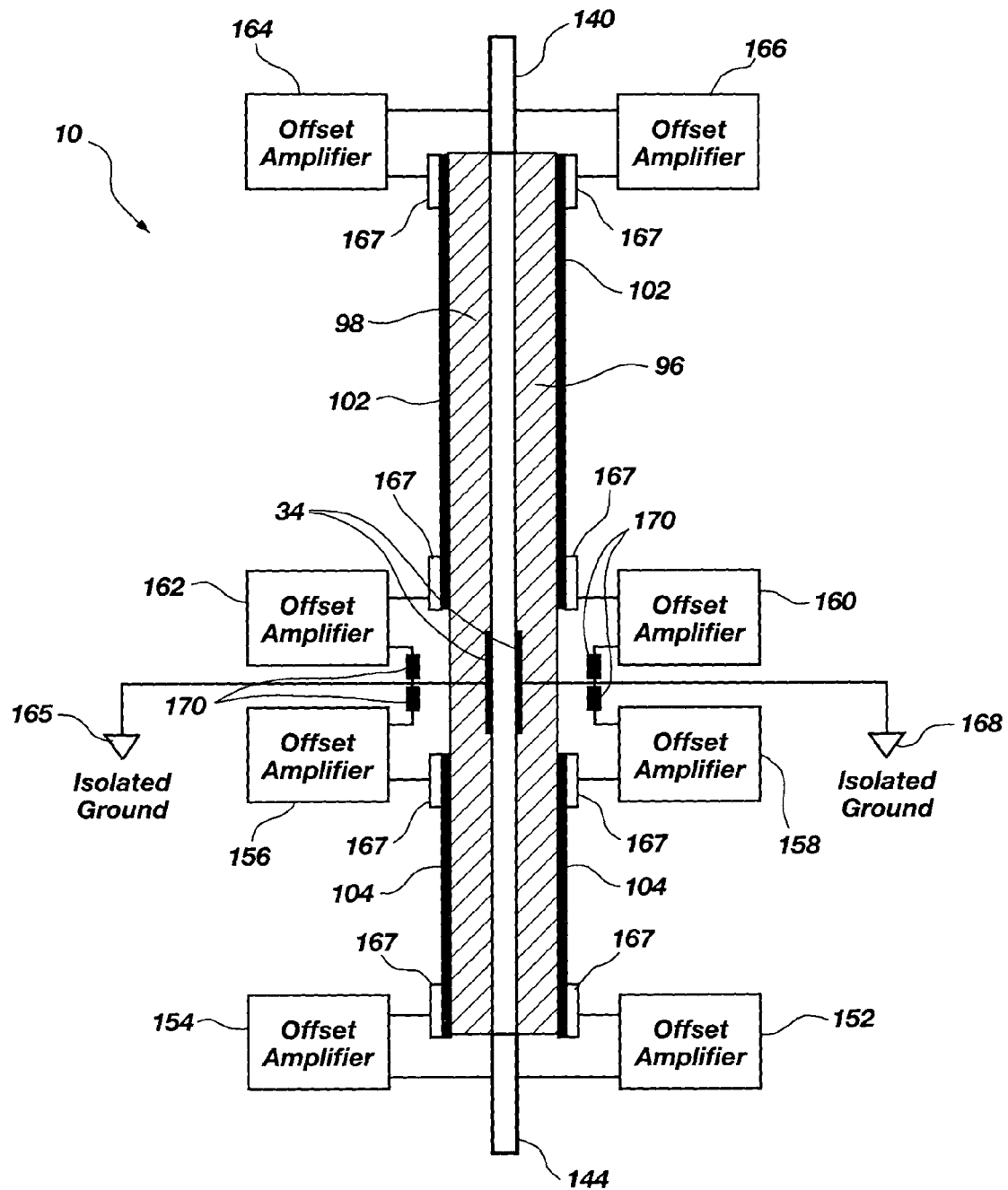
FIG. 11 is a schematic cross-sectional view of a system in accordance with principles of the invention illustrating provisions for control of electroosmotic flow.

With reference to FIG. 11, further details of the system 10 will be apparent. Control of the fluid flow velocities in the various channels is important as will be apparent from the forgoing. This is done by offsetting the voltages on the distributed resistors on either side of the channel by a certain amount, which can be a fixed amount, to generate a bound charge on the channel walls. This in turn generates a zeta potential resulting in a controlled electroosmotic flow in the channel as set forth in the parent application. In the present system 10, for example, offset amplifiers 152, 154, 156, 158, 160, 162, 164 and 166 are provided, associated with Legs 1 and 3 comprising the inlet 20 and outlet 22 channels. The offset amplifiers are connected by thick film conductors 167 on either end of each distributed resistor 102, 104 and work together to generate a constant offset voltage relative to that of the electrolyte in each leg. In the illustrated embodiment two offset amplifiers for the upper and lower distributed resistors adjacent the legs are provided. However, in another embodiment one offset amplifier can be used to drive both the upper and lower distributed resistor. To keep the electric field intensity constant for x=2 mm in the flow field, an isolated ground 168 has been added to the outside of the contour resistors at that location in the illustrated embodiment, which is in turn referenced to the offset amplifier(s). It should be noted that the reference to the isolated ground from the offset amplifier(s) can be made through a resistor(s) 170 that approximates that portion of the channel resistance that the resistor is shunting, thereby limiting the amount of drive voltage needed by the offset amplifier(s)). The isolated ground reference prevents the equilibrium point from wandering within the separation flow field cross section. The reference is attached to the outboard portion of the contour resistor corresponding to the point x=2 mm. The offset amplifiers are fed optically isolated digital bias data from a central control computer (not shown) to control the EOF.

The offset amplifiers 152, 154, 164, 166 at the upper and lower ends of the channel 52 comprising a composite of legs 1 and 3 together with the chamber 50, interface to the upper and lower electrodes (62, 62 in FIG. 7) This is done either by connecting directly to the power supply electrode in the reservoir or by connection to the Kovar tubes 140, 144. (The Kovar tubes are displaced in the drawing figure for clarity of presentation).

With reference to FIGS. 1–3 and 10, in another embodiment the system 10 is configured without the distributed resistors 102, 104, 106, 108, 110, 112 on each substrate to generate the EOF, and without the dielectric layers 96, 98. The distributed resistor is deposited directly on the substrates 90, 92. The spacer 94 defines the channels and provides a dielectric layer between the substrates. The flow components 18a,b and 24a,b,c,d corresponding with $V_{1-6}$ can be provided solely by precision pumps. This reduces costs significantly over the other embodiments discussed, and only the contour resister 34 is deposited directly on the substrates 90, 92. Otherwise the system is made substantially in accordance with the foregoing discussions. This simplification can be advantageous, particularly in a disposable embodiment.

Moreover, at least as to $V_1$ and $V_3$ the pumps can be ganged together to form a push/pull (pressure/vacuum) flow regime. For example, such a precision push-pull pump, comprising ganged syringe pumps and denominated Product No. SP120p, is available from World Precision Instruments of Sarasota Fla. In one embodiment a second precision pump is configured to provide $V_2$. A counterpart flow divided into and comprising $V_4$, $V_5$, and $V_6$ flows through several centimeters of path length in each one of the downstream rejection channel 32, the target channel 30, and upstream rejection channel 28, to exit at atmospheric pressure. In one embodiment the flow component 24 in the y-direction is kept small enough that differences in pressure drop along the target channel and rejection channels due to relative differences in size or outlet arrangements is negligible and not a factor in the separation. In another embodiment the target channel and rejection channels are configured in relation to the magnitude of the flow so that there is a difference in pressure drop influencing the separation, for example directing relatively more or less flow into a particular channel 28, 30 or 32 compared with the others.

This latter-described embodiment is particularly cost effective in a disposable as complexity is moved off the substrates 90, 92 and onto the non-disposable portions of the instrument. It will be appreciated that the syringes and fluid connections can be disposables also, but are of relatively low cost.

From the foregoing it will be apparent that the system 10 enables efficient separation of analyte species, and doing so on a continuous bases. This enables separations in many research and commercial applications which heretofore were not practicable.

It is to be understood that the above-described arrangements are only illustrative of the application of the principles of the present invention. Numerous modifications and alternative arrangements may be devised by those skilled in the art without departing from the spirit and scope of the present invention and the appended examples are intended to cover such modifications and arrangements. Thus, while the present invention has been shown in the drawings and fully described above with particularity and detail in connection with what is presently deemed to be the most practical and preferred embodiment(s) of the invention, it will be apparent to those of ordinary skill in the art that numerous modifications, including, but not limited to, variations in size, materials, shape, form, function and manner of operation, assembly and use may be made, without departing from the principles and concepts of the invention.

The invention claimed is:

1. An analyte species separation system configured to separate analyte species of different mobilities, comprising:
   a separation fluid flow field disposed between confining surfaces;
   a fluid medium flowing through the fluid flow field in a first direction;
   an analyte injector in fluid communication with the fluid flow field disposed to inject a fluid flow containing an analyte sample comprising different analyte species into the fluid flow field to enable a fluid flow component in the flow field to flow therein in a direction having a vector component in a second direction transverse to the first direction;
   a distributed resistor coupled to at least one of the confining surfaces and configured to produce an electric field having a non-linear electric field intensity contour to cause the analyte species to move in the fluid flow field in a direction opposite to the first direction, wherein analyte species of different mobilities are separated spatially along the first direction while moving through the fluid flow field in the second direction; and
   a collector disposed opposite the analyte injector and in fluid flow communication with the fluid flow field configured to receive at least a portion of the separated analyte species.

2. An analyte species separation system as set forth in claim 1, wherein the collector is disposed to collect a desired analyte species having a mobility within a selected range.

3. An analyte species separation system as set forth in claim 2 wherein an intensity gradient profile of the electric field is configured to have a relatively flatter profile slope taken in the first direction over a range corresponding with a mobility range of the desired analyte species, and a steeper slope taken in the first direction corresponding with mobilities outside of said range.

4. An analyte species separation system as set forth in claim 1, further comprising at least a second collector to receive a second portion of the separated analyte species.

5. An analyte species separation system as set forth in claim 1, further comprising a fluid pump flow generator configured to generate the flow component of the fluid medium in the first direction.

6. An analyte species separation system as set forth in claim 1, further comprising an electrical voltage potential configured to generate the flow component of the fluid medium in the first direction.

7. An analyte species separation system as set forth in claim 1, wherein the system is configured to enable the fluid medium to flow continuously to provide the flow component in the first direction and the analyte injector to continuously inject fluid comprising the analyte sample with a flow component in a second direction, so that the collector can continuously receive at least a portion of the separated analyte species.

8. An analyte species separation system as set forth in claim 1, further comprising a second stage, and wherein the collector is in fluid communication with a second injector of analyte species feeding into the second stage of the analyte species separation system.

9. An analyte species separation process for separating analyte species of different mobilities, comprising:
   providing a separation fluid flow field disposed between confining surfaces;
   directing a fluid medium to flow through the fluid flow field to provide a flow component in a first direction;
   injecting an analyte sample of different analyte species into the fluid flow field to provide a second flow component in a second direction transverse to the first direction;
   applying an electric field through a distributed resistor to produce a non-linear electric field intensity contour to cause the analyte species to move in the fluid flow field in a direction opposite to the first direction, wherein analyte species of different mobilities are separated spatially along the first direction while moving through the fluid flow field in the second direction; and
   collecting at least a portion of the separated analyte species, having a first mobility, from the fluid flow field at a location where the separated analyte species migrates to due to forces on the analyte species arising from the first and second flow components and the electric field.

10. The analyte species separation process of claim 9, wherein the collection step comprises collecting a desired analyte species having a mobility within a selected range.

11. The analyte species separation process of claim 10, wherein the electrical field is applied in the electric field application step so as to have an intensity gradient profile in the first direction having a slope of substantially zero at a point substantially corresponding to a balance between the first analyte mobility and the first flow component.

12. The analyte species separation process of claim 9, further comprising collecting at least a second separated analyte species having a second mobility different from the first mobility.

13. The analyte species separation process of claim 9, further comprising providing a fluid pump flow generator configured to generate the flow component of the fluid medium in the first direction.

14. The analyte species separation process of claim 9, further comprising providing an electrical voltage potential configured to generate an electroosmotic flow corresponding with the first flow component of the fluid medium in the first direction.

15. The analyte species separation process of claim 9, further comprising providing for the fluid medium to flow continuously in the flow field to provide a first flow component in the first direction, and for the analyte injector to continuously inject a fluid comprising the analyte sample to continuously provide a second flow component in the flow field in the second direction transverse to the first direction, so that the collector continuously receives at least a portion of the separated analyte species.

16. The analyte species separation process of claim 9, further comprising providing a second stage in the process substantially the same as that set forth above, and taking the collected portion of the separated analyte species and injecting it into the second stage.

17. An analyte species separation system configured to separate an analyte species of interest from other analyte species in an analyte sample containing a plurality of species, comprising:
- a separation flow field in a fluid medium disposed between a first confining surface and a second confining surface, said flow field having a first flow component flowing in a first direction and a second flow component flowing in a second direction, said second direction being transverse to said first direction;
- a distributed resistor coupled to at least one of the first confining surface and the second confining surface and configured to produce an electric field having a non-linear electric field intensity contour to cause analyte species to move in the separation flow field in a direction opposite to the first direction;
- an analyte separation target channel adjacent and in fluid communication with the flow field;
- an analyte injection channel in fluid communication with the flow field, said analyte injection channel being disposed so that an analyte sample injected into the flow field from the analyte injection channel traverses at least a portion of the flow field toward the target channel in a direction having a vector component parallel with the second direction, and said second flow component of the flow field flowing from the analyte injection channel toward at least the target channel;
- the system enabling analyte species to be moved in relationship to each other in directions parallel to the first direction by interaction of the first flow component and the electric field, the amount of movement being related to the mobility of the respective analyte species in the fluid medium under influence of the electric field, said analyte species being moved so as to be separated spatially in directions parallel to the first direction, and also move in the second direction through the flow field so that analyte species having mobilities outside a selected mobility range do not enter the target channel and an analyte species of interest having a mobility within a selected range is directed to, and enters, the target channel.

18. An analyte species separation system as set forth in claim 17, further comprising at least one separation rejection channel in fluid communication with the flow field and disposed adjacent the target channel so that at least some analyte species having mobilities outside the selected mobility range are directed into the separation rejection channel.

19. An analyte species separation system as in claim 18, wherein the rejection channel is disposed so as to receive analyte species with mobilities higher than the selected range.

20. An analyte species separation system as set forth in claim 19, comprising at least two rejection channels, said target channel being disposed intermediate the at least two rejection channels, whereby the system enables analyte species having mobilities above and below the selected mobility range to flow into the at least two rejection channels.

21. An analyte species separation system as set forth in claim 17, wherein the electric field comprises further comprises an electric field intensity gradient in the first direction.

22. An analyte species separation system as set forth in claim 21, wherein the electric field intensity gradient further comprises an electric field intensity gradient continuum in the first direction.

23. An analyte species separation system as set forth in claim 22, further comprising an electric field intensity gradient continuum having a profile with a center inflection along a direction parallel with the first direction.

24. An analyte species separation system as set forth in claim 17, further comprising an electroosmotic flow generator configured to generate the first flow component.

25. An analyte species separation system as set forth in claim 17, further comprising a fluid pump flow generator configured to generate the first flow component.

26. An analyte species separation system as set forth in claim 25, where the fluid pump comprises a syringe pump.

27. An analyte species separation system as set forth in claim 17, further comprising an electroosmotic flow generator configure to generate the second flow component.

28. An analyte species separation system as set forth in claim 17, further comprising a fluid pump flow generator configured to generate the second flow component.

29. An analyte species separation system as set forth in claim 26, wherein the fluid pump comprises a syringe pump.

30. An analyte species separation system as set forth in claim 17, further comprising:
- a first inflow channel in fluid communication with the flow field and configured to provide an inflow of the first flow component in the flow field;
- a first outflow channel in fluid communication with the flow field and configured to receive an carry the first flow component out of the flow field.

31. An analyte species separation system as set forth in claim 30, further comprising a first flow generator configured to generate the first flow component, said first flow generator being disposed in fluid communication in at least one of the first inflow and the first outflow channels.

32. An analyte species separation system as set forth in claim 17, further comprising a second flow generator configured to generate the second flow component, said second flow generator being disposed in fluid communication with the analyte injection channel.

33. An analyte species separation system as set forth in claim 32, wherein said second flow generator further comprises an electroosmotic flow generator.

34. An analyte species separation system as set forth in claim 32, wherein said second flow generator further comprises a fluid pump.

35. An analyte species separation system as set forth in claim 34, wherein the fluid pump comprises a syringe pump.

36. An analyte species separation system configured to separate an analyte species of interest from other analyte species in an analyte sample, comprising:
- a separation flow field in a fluid medium disposed between a first confining surface and a second confining surface, said flow field having a first flow component flowing in a first direction and a second flow component flowing in a second direction, said second direction being transverse to said first direction;
- a distributed resistor coupled to at least one of the first confining surface and the second confining surface and configured to produce an electric field having a non-linear electric field intensity contour to cause analyte species to move in the separation flow field in a direction opposite to the first direction;
- an analyte separation target channel adjacent and in fluid communication with the flow field;

at least one analyte separation channel laterally adjacent and in fluid communication with the flow field and adjacent said target channel;

an analyte injection channel in fluid communication with the flow field, said analyte injection channel being disposed so that an analyte sample injected into the flow field from the analyte injection channel traverses the flow field toward the target channel in a direction having a vector component parallel with the second direction, and said second flow component of the flow field flowing from the analyte injection channel toward at least the target channel;

the system enabling analyte species to be moved in relationship to each other in directions parallel to the first direction by interaction of the first flow component and the electric field, the amount of movement being related to the mobility of the respective analyte species in the fluid medium under influence of the electric field, said analyte species being moved so as to be separated spatially in directions parallel to the first direction and also move in the second direction through the flow field so that at least one analyte species having a mobility outside a selected mobility range enters the rejection channel, and an analyte species of interest having a mobility with the selected mobility range is directed into the target channel.

37. An analyte species separation system configured to separate an analyte species of interest from other analyte species in an analyte sample, comprising:

a separation flow field in a fluid medium disposed between a first confining surface and a second confining surface, said flow field having a first flow component flowing in a first direction and a second flow component flowing in a second direction, said second direction being transverse to said first direction;

a distributed resistor coupled to at least one of the first confining surface and the second confining surface and configured to produce an electric field having a non-linear electric field intensity contour to cause analyte species to move in the separation flow field in a direction opposite to the first direction;

an analyte separation target channel adjacent and in fluid communication with the flow field, a plurality of analyte separation rejection channels adjacent and in fluid communication with the flow field and adjacent said target channel, the target channel being disposed intermediate the rejection channels;

an analyte injection channel in fluid communication with the flow field, said analyte injection channel being disposed so that an analyte sample injected into the flow field from the analyte injection channel traverses the flow field toward the target channel in a direction having a vector component parallel with the second direction, and said second flow component of the flow field flowing from the analyte injection channel toward at least the target channel;

the system enabling analyte species to be moved in relationship to each other with a movement direction component parallel to the first direction by interaction of the first flow component and the electric field, the amount of movement of analyte species being related to the mobility of the respective analyte species in the fluid medium under influence of the electric field, said analyte species being moved so as to be separated spatially along the first direction while being moved in the second direction through the flow field so that at least two analyte species having mobilities outside a selected mobility range enter the rejection channels, and an analyte species of interest having a mobility within a selected range is directed into the target channel.

38. A method of separating an analyte species of interest from other analyte species in an analyte sample, comprising the steps of:

providing a separation flow field in a fluid medium disposed between a first confining surface and a second confining surface, said flow field having a first flow component flowing in a first direction and a second flow component flowing in a second direction, said second direction being transverse to said first direction;

applying an electric field through a distributed resistor to produce a non-linear electric field intensity contour to cause analyte species to move in the separation flow field in a direction opposite to the first direction;

providing an analyte separation target channel adjacent and in fluid communication with the flow field;

providing an analyte injection channel in fluid communication with the flow field, said analyte injection channel being disposed so that an analyte sample injected into the flow field from the analyte injection channel traverses the flow field toward the target channel in a direction having a vector component parallel with the second direction, and said second flow component of the flow field flowing from the analyte injection channel toward at least the target channel;

enabling the analyte species to be moved in relationship to each other in directions parallel to the first direction by interaction of the first flow component and the electric field, the amount of movement being related to the mobility of the respective analyte species in the fluid medium under influence of the electric field, said analyte species being moved so as to be separated spatially in directions parallel to the first direction and also move in the second direction through the flow field so that at least one analyte species having a mobility outside a selected mobility range enters the rejection channel, and an analyte species of interest having a mobility with a selected range is directed into the target channel.

39. The method of claim 38, further comprising the step of providing a fluid flow generator configured to create at least one of the first and second flow components.

40. The method of claim 39, further comprising the step of configuring the fluid flow generator to generate electroosmotic flow.

41. The method of claim 40, further comprising the step of controlling the fluid flow using a voltage applied to a control surface.

42. The method of claim 39, further comprising the steps of:

providing a fluid flow generator comprising a fluid pump; and, controlling the fluid output of the pump to control one of the first and second flow components.

43. The method of claim 38, further comprising the step of providing an electric field intensity gradient continuum, said electric field having an intensity profile taken along the first direction which is a smooth function.

44. The method of claim 38, further comprising the step of providing an electric field intensity profile in the first direction that comprises a sudden change in slope.

45. The method of claim 38, further comprising the step of providing an electric field intensity profile in the first direction that is discontinuous, providing at least one step in the profile.

46. The method of claim 38, further comprising the steps of providing at least one analyte separation rejection channel adjacent and in fluid communication with the flow field and adjacent said target channel, and receiving analyte species having a mobility different than a selected mobility within said rejection channel.

47. The method of claim 38, further comprising the steps of providing a plurality of process stages and taking fluid comprising separated analyte species from the target channel and injecting it into an injection channel of a second stage.

48. The method of claim 38, further comprising the step of providing a multiplicity of stages to provide increased selectivity of analyte species.

* * * * *